United States Patent
Zhou et al.

(10) Patent No.: US 8,822,686 B2
(45) Date of Patent: Sep. 2, 2014

(54) IRIDIUM-CONTAINING ORGANIC ELECTROLUMINESCENT MATERIAL, PREPARATION METHOD AND ORGANIC ELECTROLUMINESCENT DEVICE THEREOF

(75) Inventors: Mingjie Zhou, Shenzhen (CN); Ping Wang, Shenzhen (CN); Juanjuan Zhang, Shenzhen (CN); Lusheng Liang, Shenzhen (CN)

(73) Assignee: Ocean's King Lighting Science & Technology Co., Ltd., Shenzhen, Guangdong (CN)

( * ) Notice: Subject to any disclaimer, the term of this patent is extended or adjusted under 35 U.S.C. 154(b) by 0 days.

(21) Appl. No.: 13/992,708

(22) PCT Filed: Dec. 30, 2010

(86) PCT No.: PCT/CN2010/080484
§ 371 (c)(1),
(2), (4) Date: Jun. 7, 2013

(87) PCT Pub. No.: WO2012/088686
PCT Pub. Date: Jul. 5, 2012

(65) Prior Publication Data
US 2013/0253198 A1    Sep. 26, 2013

(51) Int. Cl.
*C07D 213/79* (2006.01)
*C07F 15/00* (2006.01)
*H01L 51/00* (2006.01)
*H05B 33/14* (2006.01)
*C09K 11/06* (2006.01)
*H01L 51/50* (2006.01)

(52) U.S. Cl.
CPC ......... *H01L 51/0085* (2013.01); *H01L 51/5016* (2013.01); *C09K 2211/1044* (2013.01); *C07F 15/0033* (2013.01); *C09K 2211/185* (2013.01); *C09K 2211/1029* (2013.01); *H05B 33/14* (2013.01); *C09K 2211/1007* (2013.01); *C09K 11/06* (2013.01)
USPC .......................................................... 546/5

(58) Field of Classification Search
None
See application file for complete search history.

(56) References Cited

U.S. PATENT DOCUMENTS

2008/0111476 A1* 5/2008 Choi et al. ................. 313/504
2010/0219406 A1* 9/2010 Kahle et al. ................. 257/40

FOREIGN PATENT DOCUMENTS

CN    101179112 A    5/2008

* cited by examiner

*Primary Examiner* — Heidi Reese
(74) *Attorney, Agent, or Firm* — Shimokaji & Associates P.C.

(57) ABSTRACT

The invention provides an iridium-containing organic electroluminescent material, the formula of which is H:

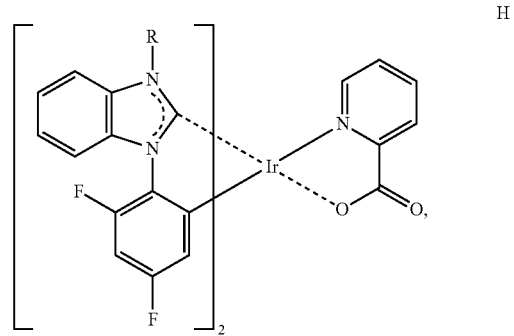

wherein R is $C_1$-$C_8$ alkyl. The molecule of the iridium-containing organic electroluminescent material contains benzimidazole group with electron transmission function and the benzimidazole has alkyl and fluorobenzyl group, which can improve the electron injection and transmission function of the electroluminescent material, and enable the electroluminescent material to have higher internal quanta efficiency and electroluminescent efficiency. The invention also provides a preparation method of the iridium-containing organic electroluminescent material, and an organic electroluminescent device using the material.

10 Claims, 2 Drawing Sheets

IRIDIUM-CONTAINING ORGANIC ELECTROLUMINESCENT MATERIAL, PREPARATION METHOD AND ORGANIC ELECTROLUMINESCENT DEVICE THEREOF

FIELD OF THE INVENTION

The invention relates to the organic electroluminescent technical field, particularly to an iridium-containing organic electroluminescent material and a preparation method thereof and an organic electroluminescent device including the same.

BACKGROUND OF THE INVENTION

Organic electroluminescent is a light-emitting phenomenon that organic materials directly convert electric energy into light energy under the effect of electric field. In early days, due to high driving voltage and low luminous efficiency of device prepared, research of organic electroluminescent was being held back. Until 1987, Tang and Van Slyke of Eastman Kodak invented thin uniform compact films of high quality using tris (8-hydroxyquinoline) aluminum ($Alq_3$) as a luminescent material together with aromatic diamine, and then prepared organic electroluminescent device of higher brightness and efficiency at relatively lower working voltage, thus started a new stage of the research of organic electroluminescent material. Theoretically, the internal quantum efficiency of fluorescent materials is merely 25%, limited by Spin Statistics theory, how to take advantage of the rest 75% brought by phosphorescent emission to obtain higher luminous efficiency has been becoming a research focus in the field. In 1997, the phosphorescent electroluminescent phenomenon was discovered by Forrest et al., after which the limit of 25% internal quantum efficiency of organic electroluminescent material was broken and the organic electroluminescent material field embraced another new stage.

In current research on organic electroluminescent materials, small molecules of doping transition metal complexes, such as iridium, ruthenium and platinum complexes have been actively researched. The advantage of the complexes is that they can obtain high emission energy from their triplet states, wherein the Ir(III) compounds have been taking a leading position in the research followed ever since for characteristics of good stability, mild synthesis reaction condition and high electroluminescent capacity. To get a full-color electroluminescent display, efficient red, green and blue electroluminescent materials with excellent performance should be available at the same time. Compared with red and green, blue electroluminescent materials are less developed, consequently, growing interests has been focused on how to improve the luminous efficiency and color saturation of blue electroluminescent materials. Iridium(III) bis[2-(4',6'-difluorophenyl)pyridinato-N,$C^2$]picolinate (FIrpic), an Ir(III) metal organic complex, is one of the most reported blue electroluminescent materials. The luminous efficiency and color saturation of the electroluminescent materials such as FIrpic and alike have been greatly improved by ligand modification and device optimization. In 2005, Holmes, Forrest et al. firstly synthesized Iridium(III) tris(1-phenyl-3-methylbenzimidazolin-2-ylidene-C,$C^{2'}$), abbreviated as Ir(pmb)$_3$, an organic electroluminescent material carrying 1-phenyl-3-methylbenzimidazolyl as the ligand, of which the CIE coordinates were (0.17, 0.06) (Applied Physics Letters. 2005, 87, 243507). Generally, 2-picolinate serves as a prior ancillary ligand for blue metal Ir(III) organic electroluminescent material, such as FIrpic and iridium(III) bis{4-phenyl-2-[6-(N-(2-methoxyl) oxethyl)ethyl)carbazolyl]quinoline}(2-picolinate) ((EO-CVz-PhQ)$_2$Ir(pic)) and etc. (Adv. Funct. Mater. 2009, 19, 2205-2212). Further more, complexes with ligands substituted by fluoro group demonstrate a greater hypochromatic shift effect than corresponding complexes without ligands, for example: Iridium(III) tris[2-(4',6'-difluorophenyl)pyridinato] (Ir($F_2$ppy)$_3$) exhibits a hypochromatic shift by 37 nm under the temperature of 77K and by 42 nm under 298K than iridium (III) tris(2-phenylpyridinato) (Ir(ppy)$_3$); iridium (III) bis[1-(4',6'-difluorophenyl)pyrazolyl](2-phenylpyridin) (($F_2$ppz)$_2$Ir(ppy)) exhibits a hypochromatic shift by 14 nm under the temperature of 77K and by 25 nm under 298K than iridium (III) bis(1-phenylpyrazolyl)(2-phenylpyridinato) ((ppz)$_2$Ir(ppy)) (J. AM. CHEM. SOC. 2009, 131, 9813-9822).

SUMMARY OF THE INVENTION

Consequently, it is necessary to provide an iridium-containing organic electroluminescent material and a preparation method thereof.

An iridium-containing an organic electroluminescent material represented by the following formula H:

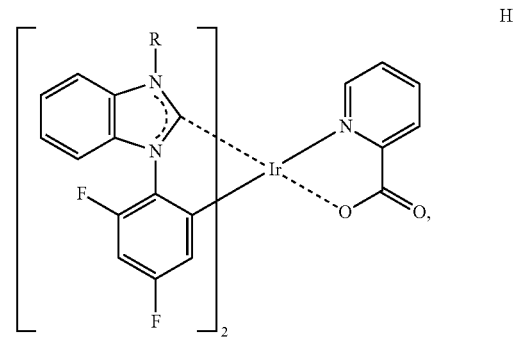

wherein R is $C_1$-$C_8$ alkyl.

The iridium-containing organic electroluminescent material exhibits a characteristic of stronger blue phosphorescent emission, which can effectively broaden the research scope of blue organic electroluminescent materials, thus providing further technical support for blue or white devices of high luminous efficiency. Besides, the molecular of said iridium-containing organic electroluminescent material comprises a benzimidazolyl with electron transmission capacity, what's more, said benzimidazolyl also carries a fluorobenzyl which can improve the electron injection and transportation capacity of the luminous material, thus bringing higher internal quanta efficiency and electroluminescent efficiency. What's more, the molecular also contains a ligand of 1-(2',4'-difluorophenyl)-3-substituted benzimidazolyl which can adjust the solubility of the compound by changing the length of alkyl chain substituted at 3-position, as a result, the compound can be better used.

A preparation method of iridium-containing organic electroluminescent materials comprising the following steps:

preparing or providing compound A and compound B represented by the following formulas:

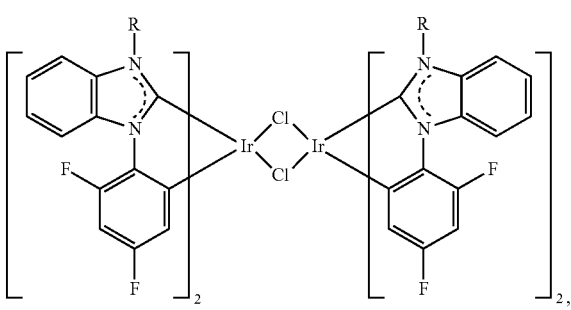

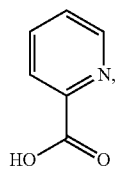

wherein R is $C_1$-$C_8$ alkyl;

caning out a reaction between compound A and compound B by heating in solvent to obtain mixture containing compound H in oxygen-free environment and in the presence of catalyst, the equation herein is as follows:

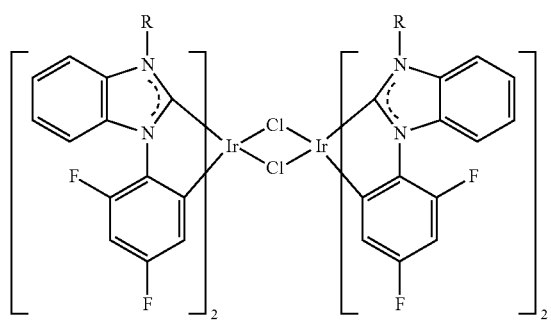

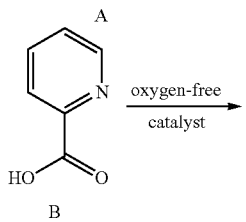

separating and purifying said mixture after cooling to obtain compound H.

Preferably, the catalyst is a weak alkaline compound, the solvent is one of 2-ethoxyethanol, 1,2-dichloroethane and dichloromethane, the reaction is reflux reaction, further preferably, the weak alkaline compound is sodium carbonate, sodium phosphate, potassium carbonate or potassium phosphate.

Preferably, said separation and purification of the mixture comprise the following steps: firstly, treating the mixture by decompression concentration, then separating the mixture obtained from decompression concentration by silica gel column chromatography using mixed solvent of ethyl acetate and hexane as eluent.

Preferably, the method of preparing compound A comprises the following steps:

step I: providing compound C and compound D represented by the following formula:

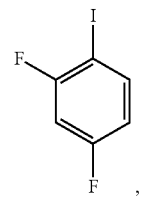

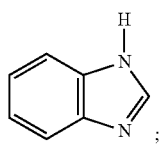

step II: carrying out a Ullmann reaction between compound C and compound D to produce compound E in oxygen-free environment and in the presence of catalyst, the equation herein is as follows:

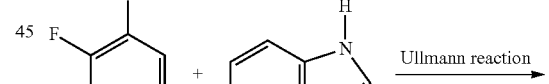

step III: carrying out a reaction between compound E produced and alkyl iodide in solvent to produce compound G, the equation herein is as follows:

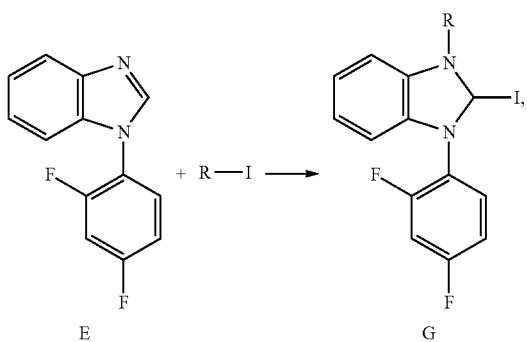

wherein R—I is alkyl iodide and R is $C_1$-$C_8$ alkyl.

step IV: carrying out a reaction between compound G and iridium trichloride hydrate in solvent to produce compound A in oxygen-free environment and in the presence of catalyst, the equation herein is as follows:

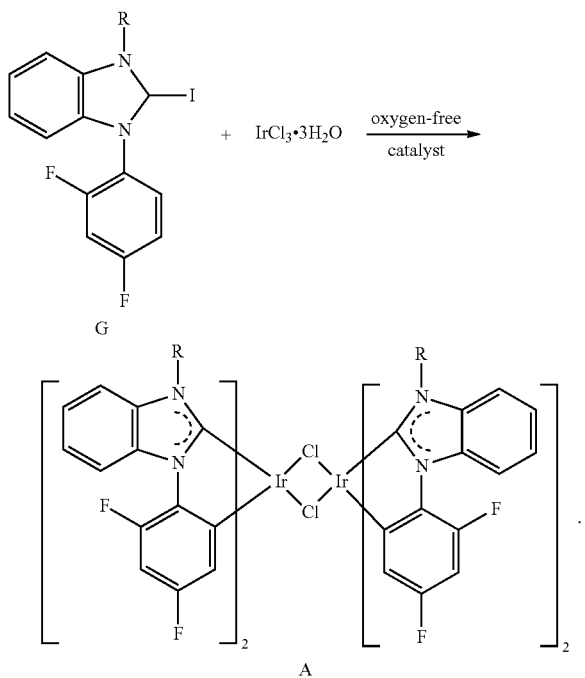

Preferably, the Ullmann reaction in step II is carried out in the temperature range of 100~180° C., using CuI or a mixture of 1,10-phenanthroline and $CeCO_3$ as catalyst and N,N-dimethylformamide as solvent; the reaction in step III is carried out in the temperature range of 25~45° C., using methylbenzene as solvent; the reaction in step IV is carried out in the temperature range of 100~150° C., using $Ag_2O$ as catalyst and 2-ethoxyethanol as solvent.

Preferably, step II is followed by further separation and purification steps of compound E, which comprise: firstly, treating the mixed liquor obtained from the Ullmann reaction by vacuum concentration; then adding ethyl acetate solution to the concentrated liquor to form precipitate; filtering and separating the precipitate, then washing the precipitate by ethyl acetate, collecting the filter liquor; finally, concentrating the filter liquor which is then separated by silica gel column chromatography using mixed solvent of ethyl acetate and hexane as eluent to obtain compound E.

Preferably, step III is followed by further separation and purification steps of compound G, which comprise: filtering the rough production of step III, then washing by methylbenzene to obtain precipitate, drying the precipitate to obtain purified compound G; said step IV is followed by further separation and purification steps of compound A, which comprise: firstly, treating the mixture liquor obtained from the reaction between compound G and iridium trichloride hydrate by decompression concentration, then separating the concentrated liquor 2~3 times by silica gel column chromatography using dichloromethane as eluent to obtain purified compound A.

With the benefits of simple principle, easy operation and low requirement for equipment, said preparation method can be widely used.

Besides, it is also necessary to provide an iridium-containing organic electroluminescent device with high internal quanta efficiency and electroluminescent efficiency.

An organic electroluminescent device including luminescent layer contains compound H represented by the following formula H:

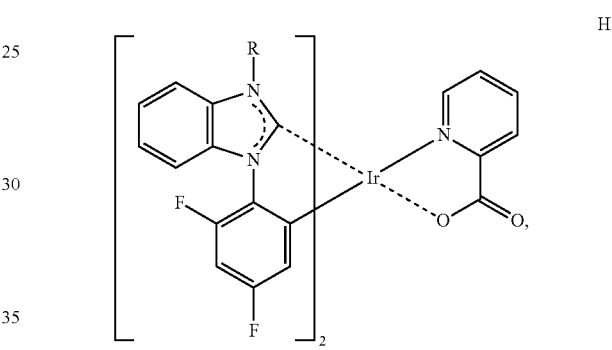

wherein R is $C_1$-$C_8$ alkyl.

Said compound H exhibits better compatibility with host materials in luminescent layer of organic electroluminescent device, thus can be widely used to prepare blue or white phosphorescent electroluminescent device. Due to better internal quanta efficiency and electroluminescent efficiency of the blue iridium-containing organic electroluminescent materials in luminescent layer, the electroluminescent device exhibits higher energy transfer efficiency and luminous efficiency consequently.

DETAILED DESCRIPTION OF ILLUSTRATED EMBODIMENTS

Below is a further detailed description of an iridium-containing organic electroluminescent material and a preparation method thereof and an organic electroluminescent device mainly by combination of drawings and detail embodiments.

Ir metal organic complex is a phosphorescent material with shorter phosphorescence lifetime (1~14 μm). The iridium-containing organic electroluminescent material in the preparation method hereof is represented by the following formula H:

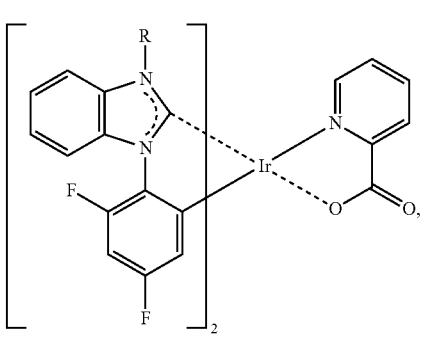

wherein R is $C_1$-$C_8$ alkyl, said alkyl can be either straight or branched alkyl such as methyl, ethyl, propyl, n-butyl, isobutyl, pentyl, isopentyl, neopentyl, hexyl, heptyl, octyl; and the like.

The molecule of the iridium-containing organic electroluminescent material of the preparation method hereof comprises a benzimidazolyl with electron-transport capacity, what's more, said benzimidazolyl also carries an alkyl and a fluorobenzyl which can improve the electron injection and transportation capacity of the luminous material, thus bringing higher internal quanta efficiency and electroluminescent efficiency. What's more, the molecular also contains a ligand of: 1-(2',4'-difluorophenyl)-3-substituted benzimidazolyl which can adjust the solubility of the compound by changing the length of alkyl chain substituted at 3-position, as a result, the compound can be better used.

The iridium-containing organic electroluminescent material exhibits a good compatible property with host materials in luminescent layer of organic electroluminescent device, thus can be widely used as a doping material to prepare blue or white phosphorescent electroluminescent device.

Figure 1:
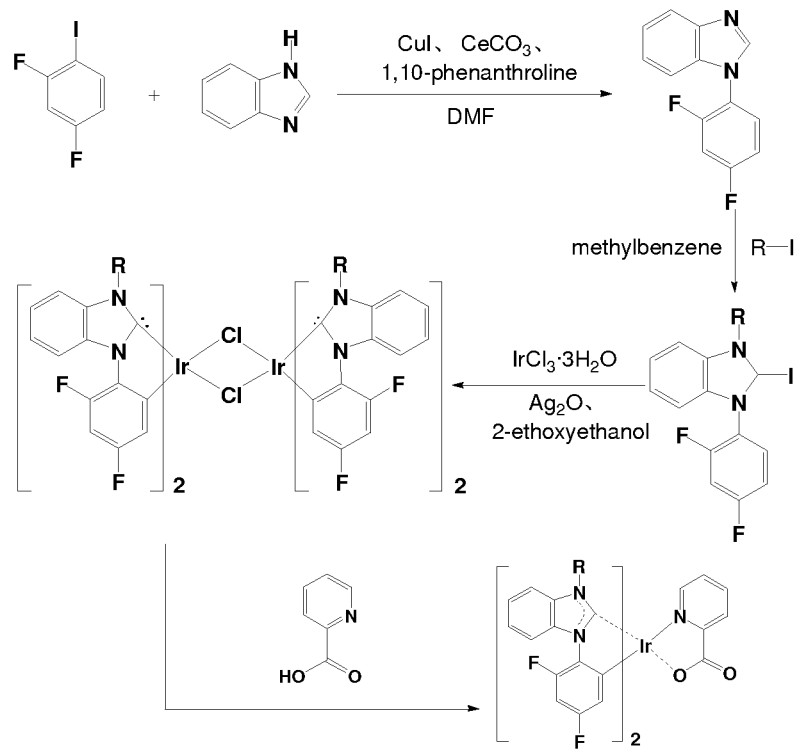
FIG. 1 is preparing process scheme of an iridium-containing organic electroluminescent material according to certain embodiment.

As shown in FIG. 1, the preparation method of said iridium-containing organic electroluminescent material can comprise the following steps:

The steps below are all performed in oxygen-free environment such as in atmosphere of nitrogen or inert gas, the solvent can be either what is used in each step or others showing good intersolubility with reactants.

step I: carrying out a Ullmann reaction between compound C (2,4-difluoroiodobenzene) and compound D (benzimidazole) to obtain compound E 1-(2',4'-difluorophenyl)benzimidazole) in the temperature range of 100~180° C. in solvent of N,N-dimethylformamide (DMF), using mixed catalyst of CuI together with 1,10-phenanthroline and $CeCO_3$, the equation herein was as follows:

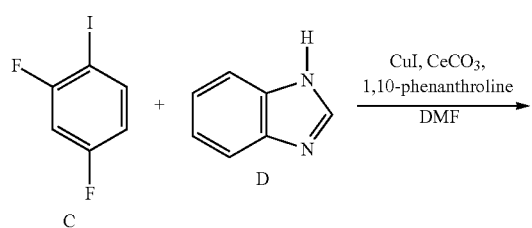

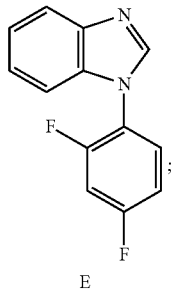

Preferable, step I was followed by further separation and purification steps of compound E, which comprised: firstly, treating the mixed liquor obtained from the Ullmann reaction by vacuum concentration; then adding ethyl acetate solution to the concentrated liquor to form precipitate; filtering the precipitate, then washing the precipitate by ethyl acetate, collecting the filter liquor; finally, concentrating the filter liquor which was then separated by silica gel column chromatography using mixed solvent of ethyl acetate and hexane as eluent to obtain compound E. The volume ratio of ethyl acetate to hexane, which was dependent on the adsorbability between compound E and the silica gel, could be different, preferably be 2:3.

step II: carrying out a reaction between compound E (2,4-difluoroiodobenzene) and alkyl iodide to produce compound G 1-(2',4'-difluorophenyl)-3-alkyl benzimidazole iodine) in the temperature range of 25~45° C. in solvent of methylbenzene, the equation herein was as follows:

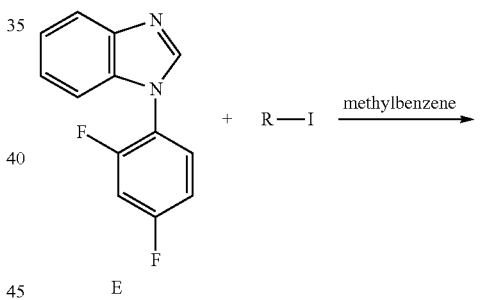

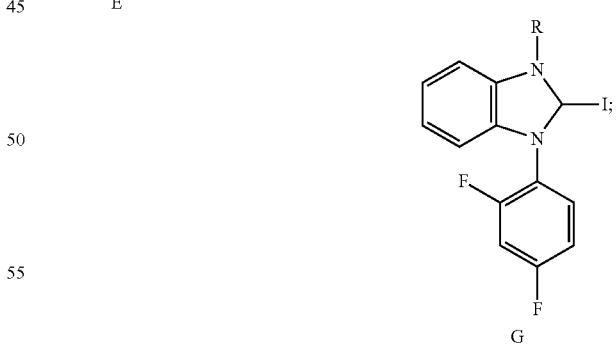

Preferably, step II was followed by further separation and purification steps of compound G, which comprised: filtering the rough production of step III, then washing by methylbenzene to obtain precipitate, drying the precipitate to obtain purified compound G.

step III: carrying out a reaction between compound G (1-(2,4-difluorophenyl)-3-alkyl benzimidazole iodine 1-(2',4'-difluorophenyl)-3-alkyl benzimidazole iodine) and iridium trichloride hydrate to produce compound A ((46df-pmb)$_2$Ir($\mu$-Cl)$_2$Ir(46dfpmb)$_2$, which were Ir(III)-chloro-bridged dimers) in the temperature range of 100~150° C., in solvent of 2-ethoxyethanol, using Ag$_2$O as catalyst, the equation herein was as follows:

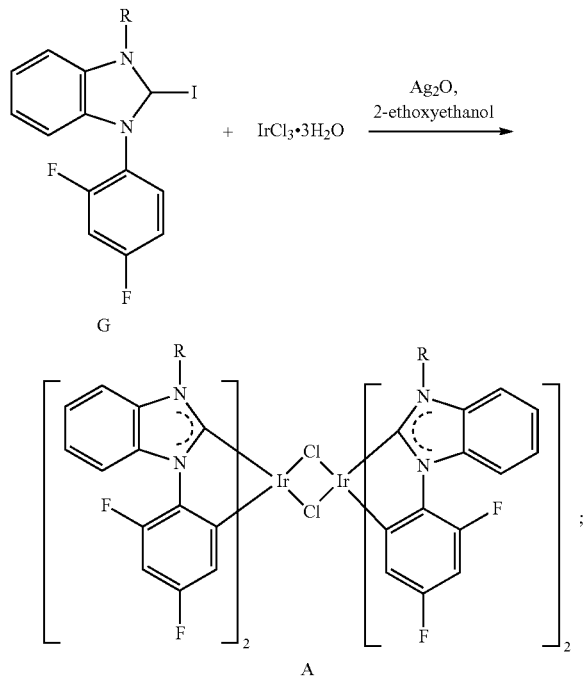

Preferable, step III was followed by further separation and purification steps of compound A, which comprised: firstly, treating the mixed liquor obtained from the reaction between compound G and iridium trichloride hydrate by decompression concentration, then separating the concentrated liquor 2~3 times by silica gel column chromatography using dichloromethane as eluent to obtain purified said compound A.

Step 4: carrying out a reaction between compound A (46df-pmb)$_2$Ir($\mu$-Cl)$_2$Ir(46dfpmb)$_2$, which were Ir(III)-chloro-bridged dimers) and compound B (2-picolinate) by heating in 1,2-dichloroethane to produce an iridium-containing organic electroluminescent material, that was, compound H (iridium (III) (bis[1-(4',6'-difluorophenyl)-3-alkyl-benzimidazolin-2-ylidene-C,C$^{2'}$](2-picolinate)) in oxygen-free environment and in the presence of catalyst using a weak alkaline compound, the equation herein was as follows:

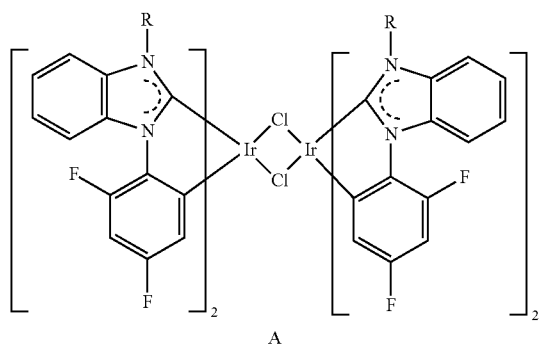

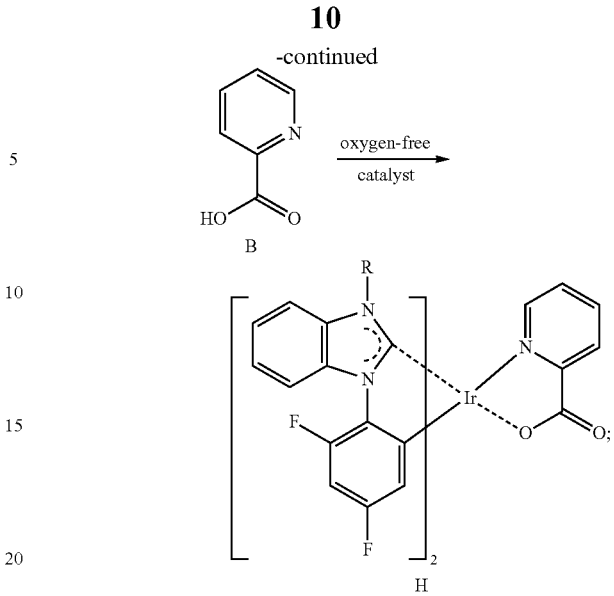

wherein the weak alkaline compound could be sodium carbonate, sodium phosphate, potassium carbonate or potassium phosphate; and the like. Alternative solvent could use organic solvent such as 1,2-dichloroethane, 2-ethoxyethanol; and the like which exhibited good compatibility with Ir(III)-chloro-bridged dimers (46dfpmb)$_2$Ir($\mu$-Cl)$_2$Ir(46dfpmb)$_2$ and 2-picolinic acid. Temperature of the reflux reaction was controlled around the solvent boiling point. Preparation of compound A could either be accomplished by referring to methods said from step II to step IV or other traditional methods.

step V: high-purity compound H iridium(III) (bis[1-(4',6'-difluorophenyl)-3-alkyl-benzimidazolin-2-ylidene-C,C$^{2'}$](2-picolinate)) could be obtained from separation and purification steps followed.

firstly, treating the mixture by decompression concentration, then separating by silica gel column chromatography using mixed solvent of ethyl acetate and hexane as eluent, preferably, the volume ratio of ethyl acetate to hexane could be 2:3.

With the benefits of simple principle, easy operation and low requirement for equipment, said preparation method can be widely used.

Below is detailed embodiments:

Example 1

Iridium(III) bis[1-(4',6'-difluorophenyl)-3-methyl-benzimidazolin-2-ylidene-C,C$^{2'}$](2-picolinate)

(1) Synthesis of Ir(III)-chloro-bridged dimers carrying benzimidazole substituted at 3-position by methyl is accomplished by referring to methods disclosed in Example 1.

To a 50-mL round bottom flask wrapped in aluminum foil, 0.16 g of CuI (0.836 mmol), 1.20 g of benzimidazole (8.36 mmol) and 5.70 g of CeCO$_3$ (17.50 mmol) were added in order, after supplying nitrogen for 15 min, 1 mL of 2,4-difluoroiodobenzene (8.36 mmol), 0.30 g of 1,10-phenanthroline (1.67 mmol) and 25 mL of anhydro N,N-dimethyl-formamide(DMF) were added into the nitrogen flow to form reaction mixed liquid; continue supplying nitrogen into the reaction mixed liquor for 30 minutes, then the reaction was held at 110° C. in oil bath with stirring for 24 hours; after cooling the reaction mixed liquid to room temperature and treating by vacuum concentration, 10 mL of ethyl acetate was added to the concentrated liquor, followed by filtering step to remove precipitate, and then washing with 30 mL of ethyl acetate and treating the filter liquor by vacuum concentration, at last, separating the filter liquor by silica gel column chromatography using mixed eluent of ethyl acetate and n-hexane (volume ratio of ethyl acetate/n-hexane=2/3) to obtain 0.924 g of bright yellow liquid containing 1-(2',4'-difluorophenyl)-benzimidazole (48% yield), the equation herein was as follows:

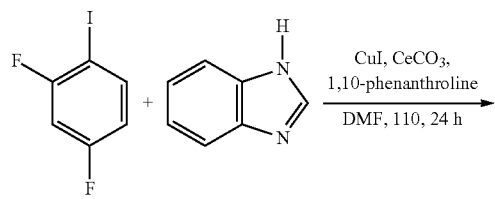

Under the protection of nitrogen, to a 25-mL round bottom flask wrapped in aluminum foil, 0.924 g of 1-(2',4'-difluorophenyl)-benzimidazole (4.013 mmol), 15 mL of methylbenzene and 1.26 g of methyl iodide (8.830 mmol) were added in order, the reaction was held for 24 hours at 30° C. with stirring to produce white precipitate; then the precipitate was filtered and washed by 20 ml of methylbenzene, at last, dried completely to obtain 0.882 g of white solid (that is, 1-(2',4'-difluorophenyl)-3-methyl-benzimidazole iodide) (59% yield), the test data of the product was: $^1$H NMR (400 MHz, CDCl$_3$, ppm): 9.32 (s, 1H), 8.31-8.13 (m, 3H), 7.78-7.66 (m, 4H), 4.52 (s, 3H), the equation herein was as follows:

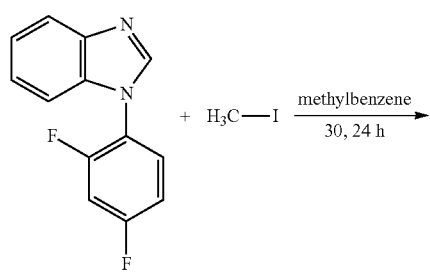

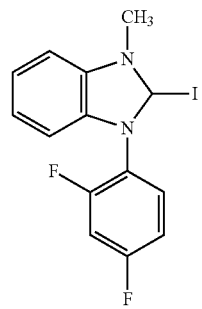

Under the protection of nitrogen, to a 100-mL round bottom flask wrapped in aluminum foil, 7.44 g of 1-(2',4'-difluorophenyl)-3-methyl-benzimidazole iodide (20.0 mmol), 5.56 g of Ag$_2$O (24 mmol), 1.77 g of iridium tritrichloride hydrate (5 mmol) and 50 mL of 2-ethoxyethanol were added in order, the reaction was held at 120° C. in oil bath for 24 hours with stirring; after cooling the mixed liquid to room temperature followed by vacuum concentration, separating twice by silica gel column chromatography using dichloromethane as eluent to obtain 0.582 g of bright yellow solid product (that is, Ir(III)-chloro-bridged dimers carrying benzimidazole substituted at 3-position by methyl) (16.3% yield), the test data of the product was: $^1$H NMR (400 MHz, CDCl$_3$, ppm): 8.33 (s, 4H), 8.14 (d, 4H), 7.81 (d, 4H), 7.75 (m, 4H), 7.67 (m, 4H), 7.38 (d, 4H), 4.49 (s, 12H), the equation herein was as follows:

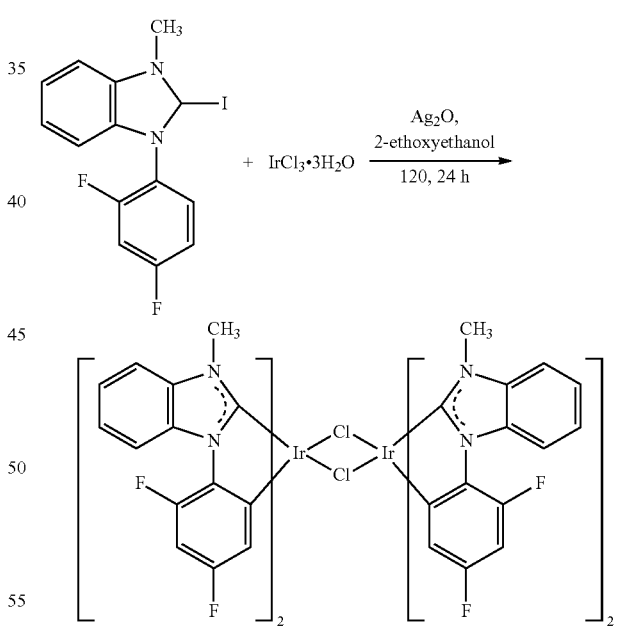

Synthesis of iridium(III) bis[1-(4',6'-difluorophenyl)-3-methyl-benzimidazolin-2-ylidene-C,C$^{2'}$](2-picolinate)

Under the protection of nitrogen, to a 50-mL three-neck round-bottom flask wrapped in aluminum foil, 0.7141 g of Ir(III)-chloro-bridged dimers carrying benzimidazole substituted at 3-position by methyl (0.5 mmol), 0.1225 g of 2-picolinic acid (1.25 mmol), 0.636 g of N$_{a2}$C$_{O3}$ (6 mmol) and 30 mL of 1,2-dichloroethane were added in order, the reflux reaction was held for 16 hours with heating. After cooling to room temperature followed by decompression concentration, separating by silica gel column chromatography using mixed eluent of ethyl acetate and n-hexane (the volume ratio of ethyl acetate/n-hexane=2/3), at last, 0.360 g of purified iridium(III) bis[1-(4',6'-difluorophenyl)-3-methyl-benzimidazolin-2-ylidene-C,C$^{2'}$](2-picolinate) (43% yield) was obtained, the equation herein was as follows:

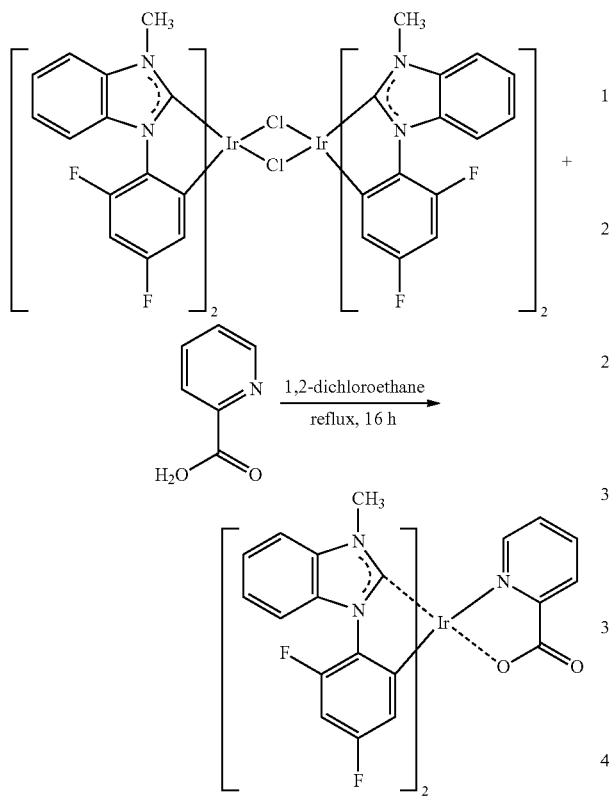

Test data of the final product was: $^1$H NMR (400 MHz, CDCl$_3$, ppm): 8.54~7.56 (m, 4H), 6.88 (s, 2H), 6.78 (s, 2H), 6.63 (m, 2H), 6.59 (m, 2H), 6.48 (d, 2H), 6.40 (d, 2H), 3.85~3.75 (m, 6H).

Emission spectrum of the final product showed a major peak at 376 nm and a shoulder peak at 396 nm at the temperature of 77K in 2-methyltetrahydrofuran solution (about $10^{-5}$ mol/L), which means that the product hereof can be widely used as a blue electroluminescent material in organic electroluminescent device preparing field.

Example 2

Iridium(III) bis[1-(4',6'-difluorophenyl)-3-ethyl-benzimidazolin-2-ylidene-C,C$^{2'}$](2-picolinate)

(1). The synthesis of Ir(III)-chloro-bridged dimers carrying benzimidazole substituted at 3-position by ethyl is accomplished by referring to methods disclosed in Example 1.

(2). Synthesis of iridium(III) bis[1-(4',6'-difluorophenyl)-3-ethyl-benzimidazolin-2-ylidene-C,C$^{2'}$](2-picolinate)

Under the protection of nitrogen, To a 50-mL three-neck round-bottom flask wrapped in aluminum foil, 0.7422 g of Ir(III)-chloro-bridged dimers carrying benzimidazole substituted at 3-position by ethyl (0.5 mmol), 0.1225 g of 2-picolinic acid (1.25 mmol), 0.636 g of Na$_2$CO$_3$(6 mmol) and 30 mL of 1,2-dichloroethane were added in order, the reflux reaction was held for 16 hours with heating. After cooling to room temperature followed by decompression concentration, separating by silica gel column chromatography using mixed eluent of ethyl acetate and n-hexane (the volume ratio of ethyl acetate/n-hexane=2/3), at last, 0.4062 g of purified iridium (III) bis[1-(4',6'-difluorophenyl)-3-ethyl-benzimidazolin-2-ylidene-C,C$^{2'}$](2-picolinate) (47% yield) was obtained, the equation herein was as follows:

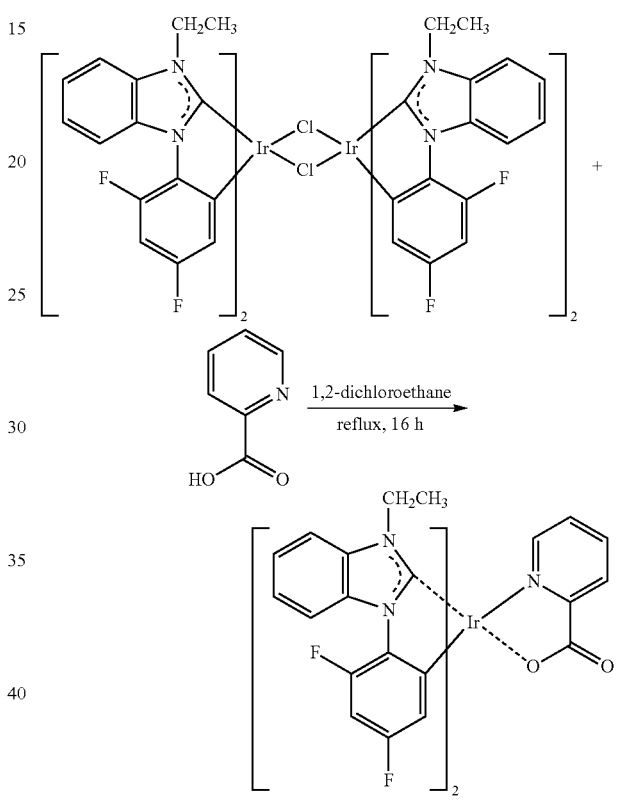

Test data of the final product was: $^1$H NMR (400 MHz, CDCl$_3$, ppm): 8.53~7.52 (m, 4H), 6.86 (s, 2H), 6.77 (s, 2H), 6.64 (m, 2H), 6.57 (m, 2H), 6.47 (d, 2H), 6.37 (d, 2H), 3.81~3.72 (m, 4H), 2.12~2.07 (m, 6H).

Emission spectrum of the final product showed a major peak at 376 nm and a shoulder peak at 396 nm at the temperature of 77K in 2-methyltetrahydrofuran solution (about $10^{-5}$ mol/L), which means that the product hereof can be widely used as a blue electroluminescent material in organic electroluminescent device preparing field.

Example 3

Iridium(III) bis[1-(4',6'-difluorophenyl)-3-propyl-benzimidazolin-2-ylidene-C,C$^{2'}$](2-picolinate)

(1). The synthesis of Ir(III)-chloro-bridged dimers carrying benzimidazole substituted at 3-position by propyl is accomplished by referring to methods disclosed in Example 1.

(2) synthesis of iridium(III) bis[1-(4',6'-difluorophenyl)-3-propyl-benzimidazolin-2-ylidene-C,C$^{2'}$](2-picolinate)

Under the protection of nitrogen, to a 50-mL three-neck round-bottom flask wrapped in aluminum foil, 0.7702 g of Ir(III)-chloro-bridged dimers carrying benzimidazole which is substituted at 3-position by propyl (0.5 mmol), 0.1225 g of 2-picolinic acid (1.25 mmol), 0.636 g of $Na_2CO_3$ (6 mmol) and 30 mL 1,2-dichloroethane were added in order, the reflux reaction was held for 16 hours with heating. After cooling to room temperature followed by decompression concentration, separating by silica gel column chromatography using mixed eluent of ethyl acetate and n-hexane (the volume ratio of ethyl acetate/n-hexane=2/3), at last, 0.4729 g of purified iridium (III) bis[1-(4',6'-difluorophenyl)-3-propyl-benzimidazolin-2-ylidene-C,$C^{2'}$](2-picolinate) (53% yield) was obtained, the equation herein was as follows:

(2) synthesis of iridium(III) bis[1-(4',6'-difluorophenyl)-3-butyl-benzimidazolin-2-ylidene-C,$C^{2'}$](2-picolinate)

Under the protection of nitrogen, to a 50-mL three-neck round-bottom flask wrapped in aluminum foil, 0.7983 g of Ir(III)-chloro-bridged dimers carrying benzimidazole substituted at 3-position by butyl (0.5 mmol), 0.1225 g of 2-picolinic acid (1.25 mmol), 0.636 g of $Na_2CO_3$ (6 mmol) and 30 mL of 1,2-dichloroethane were added in order, the reflux reaction was held for 16 hours with heating. After cooling to room temperature followed by decompression concentration, separating by silica gel column chromatography using mixed eluent of ethyl acetate and n-hexane (the volume ratio of ethyl acetate/n-hexane=2/3), at last, 0.4510 g of purified iridium (III) bis[1-(4',6'-difluorophenyl)-3-butyl-benzimidazolin-2-ylidene-C,$C^{2'}$](2-picolinate) (49% yield) was obtained, the equation herein was as follows:

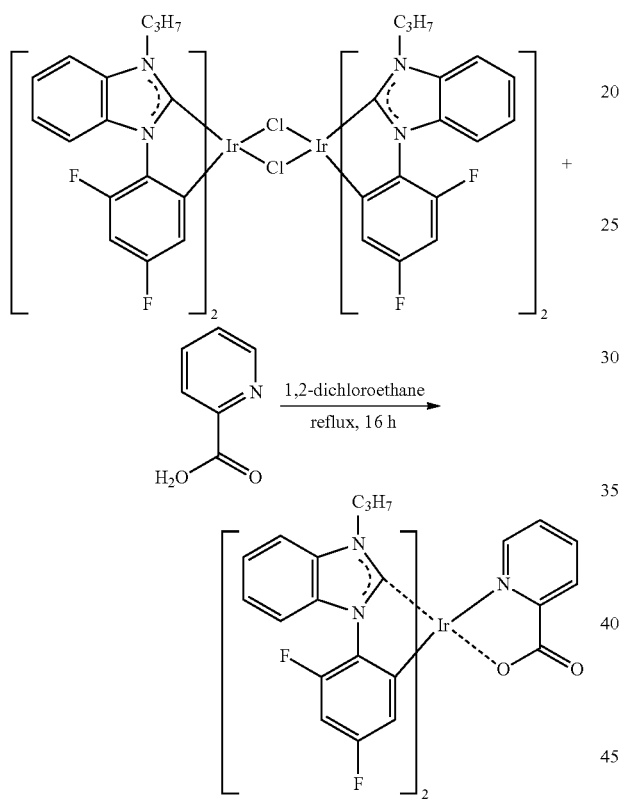

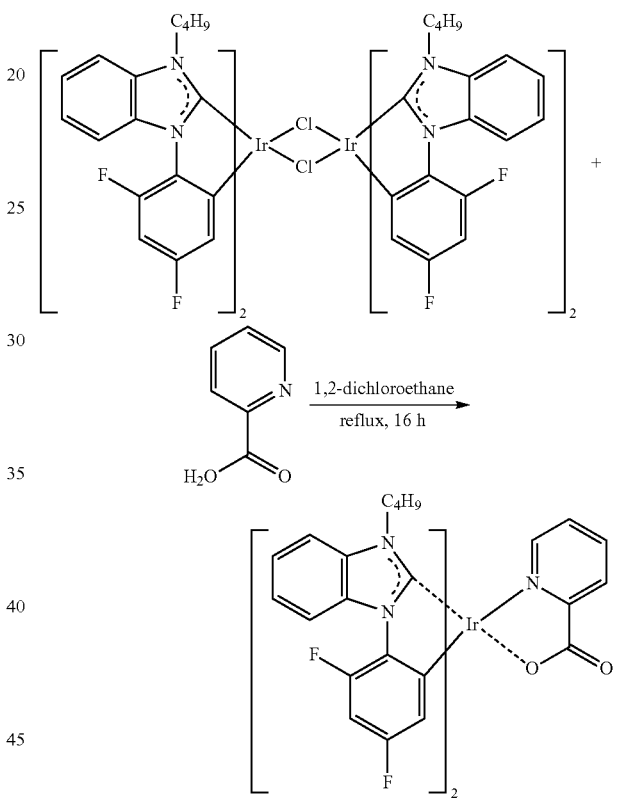

Test data of the final product was: $^1$H NMR (400 MHz, $CDCl_3$, ppm): 8.52~7.48 (m, 4H), 6.85 (s, 2H), 6.76 (s, 2H), 6.64 (m, 2H), 6.55 (m, 2H), 6.46 (d, 2H), 6.38 (d, 2H), 3.81~3.73 (m, 4H), 2.12~1.32 (m, 10H).

Emission spectrum of the final product showed a major peak at 377 nm and a shoulder peak at 397 nm at the temperature of 77K in 2-methyltetrahydrofuran solution (about $10^{-5}$ mol/L), which means that the product hereof can be widely used as a blue electroluminescent material in organic electroluminescent device preparing field.

Test data of the final product was: $^1$H NMR (400 MHz, $CDCl_3$, ppm): 8.51~7.45 (m, 4H), 6.83 (s, 2H), 6.74 (s, 2H), 6.63 (m, 2H), 6.55 (m, 2H), 6.47 (d, 2H), 6.36 (d, 2H), 3.83~3.73 (m, 4H), 2.11~0.99 (m, 14H).

Emission spectrum of the final product showed a major peak at 377 nm and a shoulder peak at 397 nm at the temperature of 77K in 2-methyltetrahydrofuran solution (about $10^{-5}$ mol/L), which means that the product hereof can be widely used as a blue electroluminescent material in organic electroluminescent device preparing field.

Example 4

Iridium(III) bis[1-(4',6'-difluorophenyl)-3-butyl-benzimidazolin-2-ylidene-C,$C^{2'}$](2-picolinate)

(1) The synthesis of Ir(III)-chloro-bridged dimers carrying benzimidazole substituted at 3-position by butyl is accomplished by referring to methods disclosed in Example 1.

Example 5

Iridium(III) bis[1-(4',6'-difluorophenyl)-3-pentyl-benzimidazolin-2-ylidene-C,$C^{2'}$](2-picolinate)

(1) The synthesis of Ir(III)-chloro-bridged dimers carrying benzimidazole substituted at 3-position by pentyl is accomplished by referring to methods disclosed in Example 1.

(2) Synthesis of iridium(III)bis[1-(4',6'-difluorophenyl)-3-pentyl-benzimidazolin-2-ylidene-C,C$^{2'}$](2-picolinate)

Under the protection of nitrogen, to a 50-mL three-neck round-bottom flask wrapped in aluminum foil, 0.8264 g of Ir(III)-chloro-bridged dimers carrying benzimidazole substituted at 3-position by pentyl (0.5 mmol), 0.1225 g of 2-picolinic acid (1.25 mmol), 0.636 g of Na$_2$CO$_3$ (6 mmol) and 30 Ml of 1,2-dichloroethane were added in order, the reflux reaction was held for 16 hours with heating. After cooling to room temperature and treating by decompression concentration, separating by silica gel column chromatography using mixed eluent of ethyl acetate and n-hexane (the volume ratio of ethyl acetate/n-hexane=2/3), at last, 0.4837 g of purified iridium(III) bis [1-(4',6'-difluorophenyl)-3-pentyl-benzimidazolin-2-ylidene-C,C$^{2'}$](2-picolinate) (51% yield) was obtained, the equation herein was as follows:

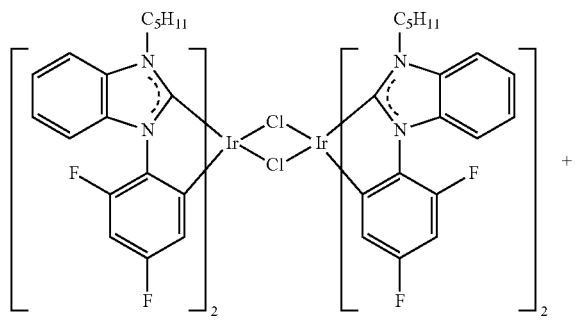

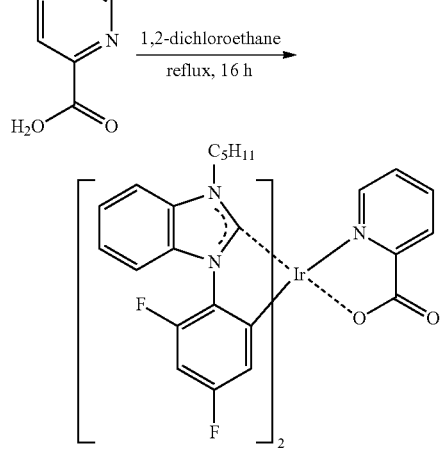

Test data of the final product was: $^1$H NMR (400 MHz, CDCl$_3$, ppm): 8.49~7.46 (m, 4H), 6.83 (s, 2H), 6.77 (s, 2H), 6.64 (m, 2H), 6.56 (m, 2H), 6.44 (d, 2H), 6.36 (d, 2H), 3.77~3.68 (m, 4H), 2.13~0.98 (m, 18H).

Emission spectrum of the final product showed a major peak at 378 nm and a shoulder peak at 398 nm at the temperature of 77K in 2-methyltetrahydrofuran solution (about 10$^{-5}$ mol/L), which means that the product hereof can be widely used as a blue electroluminescent material in organic electroluminescent device preparing field.

Example 6

Iridium(III) bis[1-(4',6'-difluorophenyl)-3-hexyl-benzimidazolin-2-ylidene-C,C$^{2'}$](2-picolinate)

(1) Synthesis of Ir(III)-chloro-bridged dimers carrying benzimidazole substituted at 3-position by hexyl is accomplished by referring to methods disclosed in Example 1.

(2) Synthesis of iridium(III) bis[1-(4',6'-difluorophenyl)-3-hexyl-benzimidazolin-2-ylidene-C,C$^{2'}$](2-picolinate)

Under the protection of nitrogen, to a 50-mL three-neck round-bottom flask wrapped in aluminum foil, 0.8544 g of Ir(III)-chloro-bridged dimers carrying benzimidazole substituted at 3-position by hexyl (0.5 mmol), 0.1225 g of 2-picolinic acid (1.25 mmol), 0.636 g of Na$_2$CO$_3$(6 mmol) and 30 mL of 1,2-dichloroethane were added in order, the reflux reaction was held for 16 hours with heating. After cooling to room temperature followed by decompression concentration, separating by silica gel column chromatography using mixed eluent of ethyl acetate and n-hexane (the volume ratio of ethyl acetate/n-hexane=2/3), at last, 0.4004 g of purified iridium (III) bis [1-(4',6'-difluorophenyl)-3-hexyl-benzimidazolin-2-ylidene-C,C$^{2'}$](2-picolinate) (41% yield) was obtained, the equation herein was as follows:

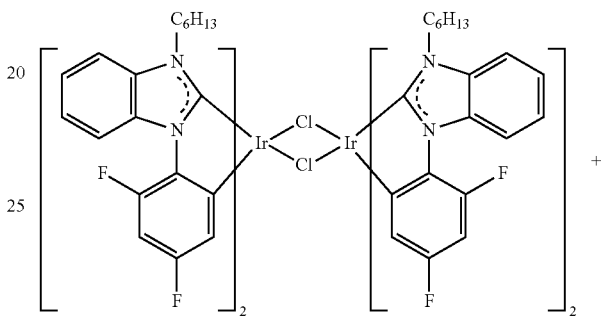

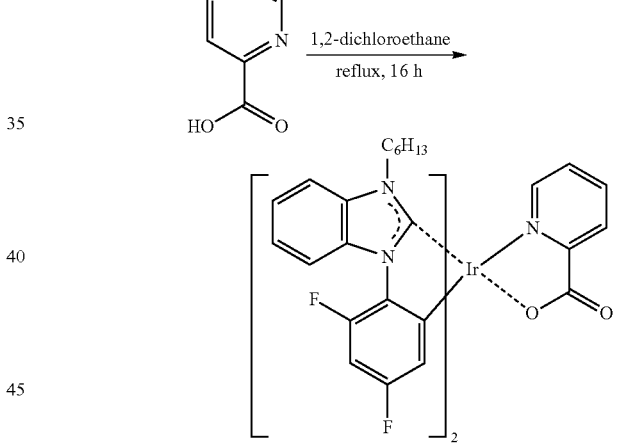

Test data of the final product was: $^1$H NMR (400 MHz, CDCl$_3$, ppm): 8.51~7.47 (m, 4H), 6.83 (s, 2H), 6.76 (s, 2H), 6.65 (m, 2H), 6.54 (m, 2H), 6.43 (d, 2H), 6.34 (d, 2H), 3.71~3.67 (m, 4H), 2.15~0.97 (m, 22H).

Emission spectrum of the final product showed a major peak at 378 nm and a shoulder peak at 398 nm at the temperature of 77K in 2-methyltetrahydrofuran solution (about 10$^{-5}$ mol/L), which means that the product hereof can be widely used as a blue electroluminescent material in organic electroluminescent device preparing field.

Example 7

Iridium(III) bis[1-(4',6'-difluorophenyl)-3-heptyl-benzimidazolin-2-ylidene-C,C$^{2'}$](2-picolinate)

(1) Synthesis of Ir(III)-chloro-bridged dimers carrying benzimidazole substituted at 3-position by heptyl is accomplished by referring to methods disclosed in Example 1.

(2) Synthesis of iridium(III) bis[1-(4',6'-difluorophenyl)-3-heptyl-benzimidazolin-2-ylidene-C,C$^{2'}$](2-picolinate)

Under the protection of nitrogen, to a 50-mL three-neck round-bottom flask wrapped in aluminum foil, 0.8825 g of Ir(III)-chloro-bridged dimers carrying benzimidazole substituted at 3-position by heptyl (0.5 mmol), 0.1225 g of 2-picolinic acid (1.25 mmol), 0.636 g of Na$_2$CO$_3$ (6 mmol) and 30 mL of 1,2-dichloroethane were added in order, the reflux reaction was held for 16 hours with heating. After cooling to room temperature followed by decompression concentration, separating by silica gel column chromatography using mixed eluent of ethyl acetate and n-hexane (the volume ratio of ethyl acetate/n-hexane=2/3), at last, 0.4018 g of purified iridium(III) bis [1-(4',6'-difluorophenyl)-3-heptyl-benzimidazolin-2-ylidene-C,C$^{2'}$](2-picolinate) (40% yield) was obtained, the equation herein was as follows:

(1) Synthesis of iridium(III) bis[1-(4',6'-difluorophenyl)-3-octyl-benzimidazolin-2-ylidene-C,C$^{2'}$](2-picolinate)

Under the protection of nitrogen, to a 50-mL three-neck round-bottom flask wrapped in aluminum foil, 0.9105 g of Ir(III)-chloro-bridged dimers carrying benzimidazole substituted at 3-position by octyl (0.5 mmol), 0.1225 g of 2-picolinic acid (1.25 mmol), 0.636 g of Na$_2$CO$_3$ (6 mmol) and 30 mL of 1,2-dichloroethane were added in order, the reflux reaction was held for 16 hours with heating. After cooled to room temperature and concentrated by way of decompression concentration, 0.3924 g of purified iridium(III) bis[1-(4',6'-difluorophenyl)-3-octyl-benzimidazolin-2-ylidene-C,C$^{2'}$](2-picolinate)(38% yield) was obtained, the equation herein was as follows:

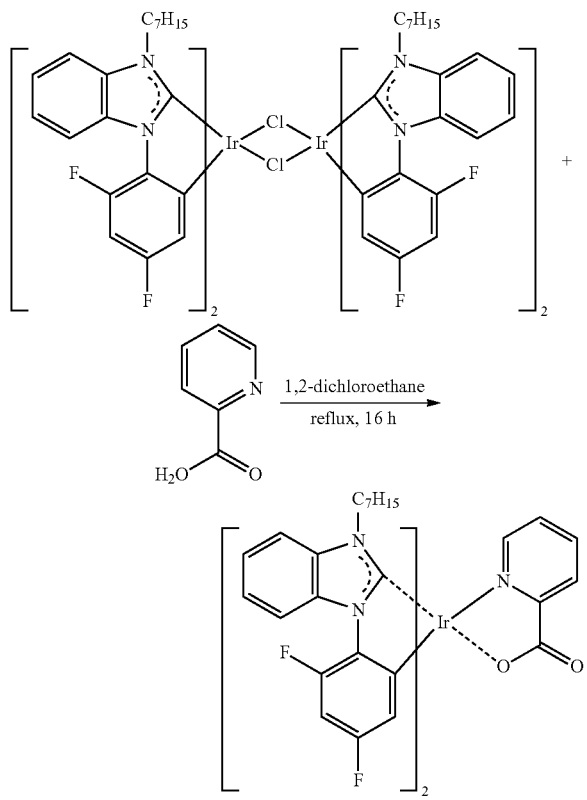

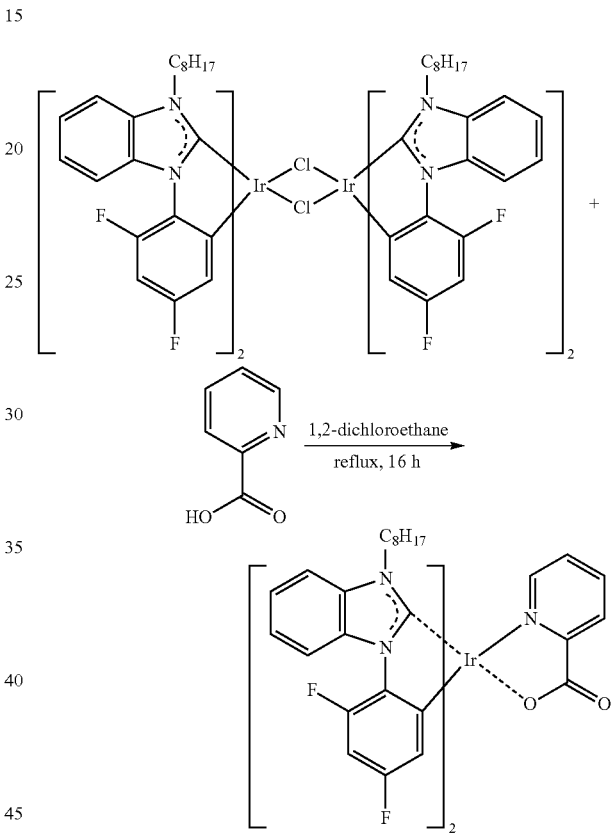

Test data of the final product was: $^1$H NMR (400 MHz, CDCl$_3$, ppm): 8.52~7.45 (m, 4H), 6.82 (s, 2H), 6.74 (s, 2H), 6.63 (m, 2H), 6.52 (m, 2H), 6.42 (d, 2H), 6.33 (d, 2H), 3.70~3.66 (m, 4H), 2.14~0.96 (m, 26H).

Emission spectrum of the final product showed a major peak at 379 nm and a shoulder peak at 399 nm at the temperature of 77K in 2-methyltetrahydrofuran solution (about 10$^{-5}$ mol/L), which means that the product hereof can be widely used as a blue electroluminescent material in organic electroluminescent device preparing field.

Example 8

Iridium(III) bis[1-(4',6'-difluorophenyl)-3-octyl-benzimidazolin-2-ylidene-C,C$^{2'}$](2-picolinate)

(1) Synthesis of Ir(III)-chloro-bridged dimers carrying benzimidazole substituted at 3-position by octyl is accomplished by referring to methods disclosed in Example 1.

Test data of the final product was: $^1$H NMR (400 MHz, CDCl$_3$, ppm): 8.51~7.43 (m, 4H), 6.81 (s, 2H), 6.72 (s, 2H), 6.631 (m, 2H), 6.51 (m, 2H), 6.40 (d, 2H), 6.31 (d, 2H), 3.66~3.51 (m, 4H), 2.13~0.95 (m, 30H).

Figure 2:
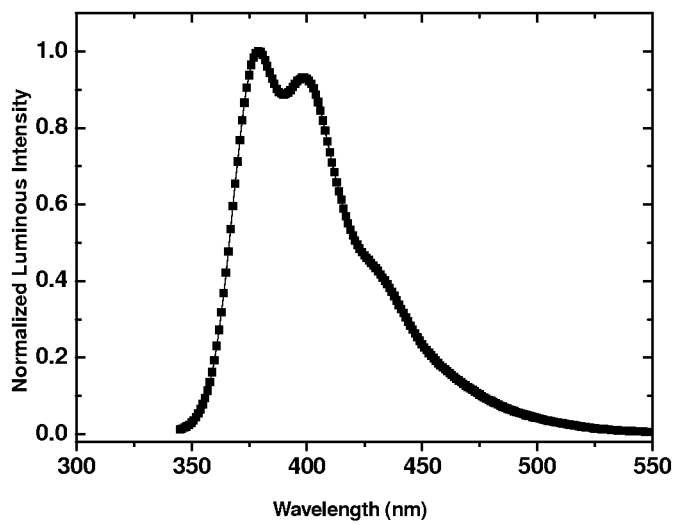
FIG. 2 is emission spectrum of the organic electroluminescent material prepared in embodiment 8.

As showed in FIG. 2, emission spectrum of the final product exhibited a major peak at 376 nm and a shoulder peak at 396 nm at the temperature of 77K in 2-methyltetrahydrofuran solution (about 10$^{-5}$ mol/L), which means that the product hereof can be widely used as a blue electroluminescent material in organic electroluminescent device preparing field.

Figure 3:
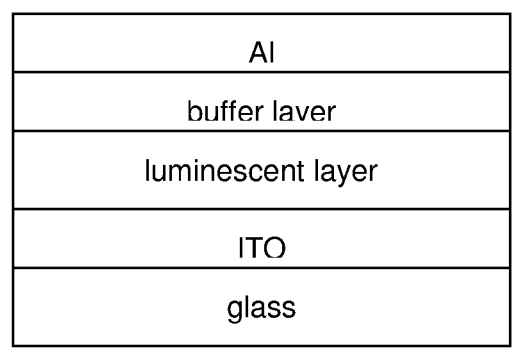
FIG. 3 is structure scheme of the organic electroluminescent device prepared in embodiment 8.

(3) An organic electroluminescent device using iridium (III) bis [1-(4',6'-difluorophenyl)-3-octyl-benzimidazolin-2-ylidene-C,C$^{2'}$](2-picolinate) (hereinafter abbr. as 46dfpmb)$_2$Irpic) prepared in the embodiment as a doping material in the luminous layer, of which the structure was showed in FIG. 3:

Said device comprised ITO/(46dfpmb)$_2$Irpic/LiF/Al in sequence, that was: depositing a layer of indium tin oxide (ITO) of which the square resistance was 10-20 Ω/mouth as the transparent anode on a glass slide, preparing a luminescent layer containing (46dfpmb)$_2$Irpic material obtained in the embodiment on ITO by spin-coating technique, on which fabricate a buffer layer of LiF by vacuum evaporation, at last, depositing metal of Al on buffer layer as cathode of the device by vacuum coating technique. Due to better internal quanta efficiency and electroluminescent efficiency of the blue iridium-containing organic electroluminescent materials in luminescent layer, the electroluminescent device exhibits higher energy transfer efficiency and luminous efficiency consequently, thus can be widely used in blue or white luminous field.

While the present invention has been described with reference to particular embodiments, it will be understood that the embodiments are illustrative and that the invention scope is not so limited. Alternative embodiments of the present invention will become apparent to those having ordinary skill in the art to which the present invention pertains. Such alternate embodiments are considered to be encompassed within the spirit and scope of the present invention. Accordingly, the scope of the present invention is described by the appended claims and is supported by the foregoing description.

What is claimed is:

1. An iridium-containing organic electroluminescent material having formula H:

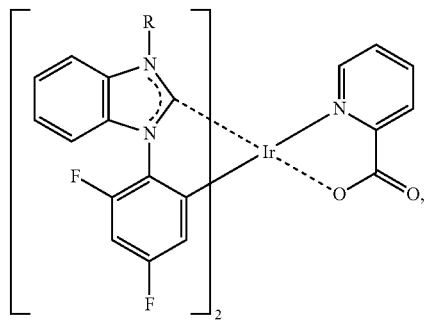

H wherein R is C1-C8 alkyl.

2. A preparation method of iridium-containing organic electroluminescent materials comprising the following steps:

preparing or providing compound A and compound B represented by the following formula:

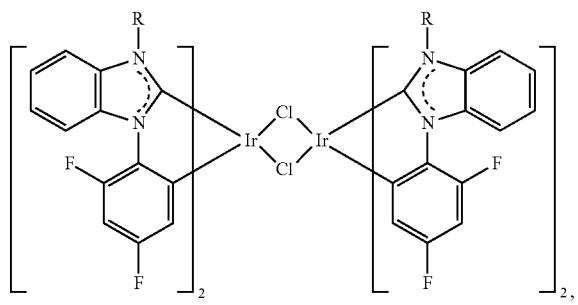

A

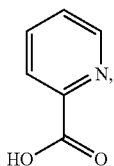

B wherein R is C1-C8 alkyl;

carrying out a reaction between said compound A and compound B by heating in solvent to obtain mixture containing compound H in oxygen-free environment and in the presence of catalyst, the equation herein is as follows:

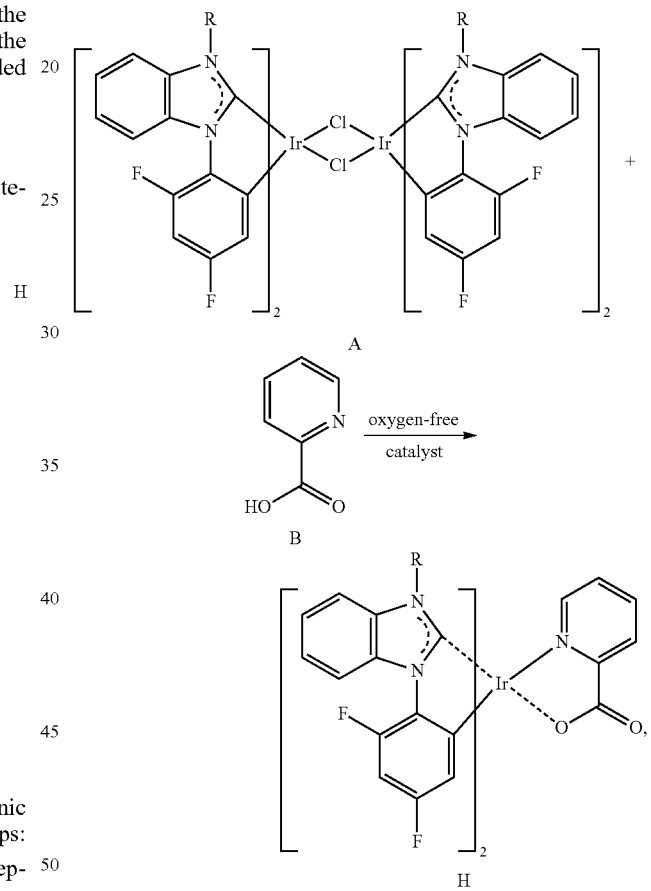

separating and purifying said mixture after cooling to obtain compound H.

3. The preparation method of iridium-containing organic electroluminescent materials according to claim 2, wherein said catalyst is a weak alkaline compound, said solvent is one of 2-ethoxyethanol, 1,2-dichloroethane and dichloromethane, said reaction is reflux reaction.

4. The preparation method of iridium-containing organic electroluminescent materials according to claim 3, wherein said weak alkaline compound is sodium carbonate, sodium phosphate, potassium carbonate or potassium phosphate.

5. The preparation method of iridium-containing organic electroluminescent materials according to claim 2, wherein the separation and purification of said mixture comprises the following steps: firstly, treating the mixture by decompression concentration, then separating the mixture obtained from decompression concentration by silica gel column chromatography using mixed solvent of ethyl acetate and hexane as eluent.

6. The preparation method of iridium-containing organic electroluminescent materials according to claim 2, wherein the process of preparing compound A comprises the following steps:

step I: providing compound C and compound D represented by the following formula:

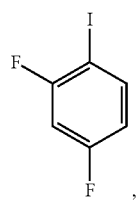
C

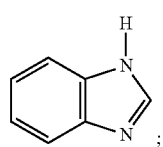
D step II: carrying out a Ullmann reaction between compound C and compound D to produce compound E in oxygen-free environment and in the presence of catalyst, the equation herein is as follows:

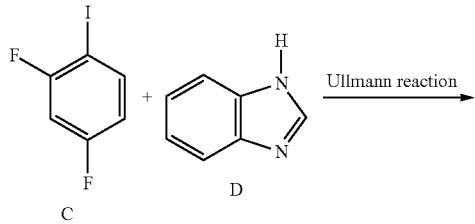

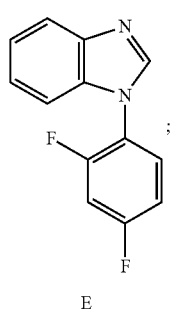
E step III: carrying out a reaction between compound E produced and alkyl iodide in solvent to produce said compound G, the equation herein is as follows:

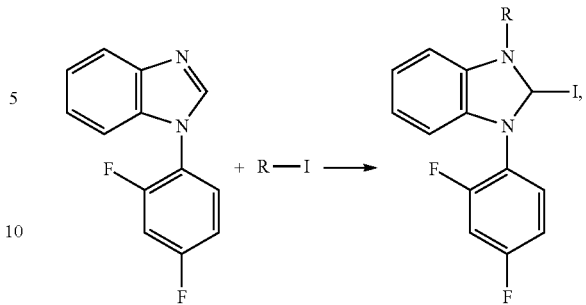

wherein R—I is alkyl iodide and R is C1-C8 alkyl;

step IV: carrying out a reaction between compound G and iridium trichloride hydrate in solvent to produce said compound A in oxygen-free environment and in the presence of catalyst, the equation herein is as follows:

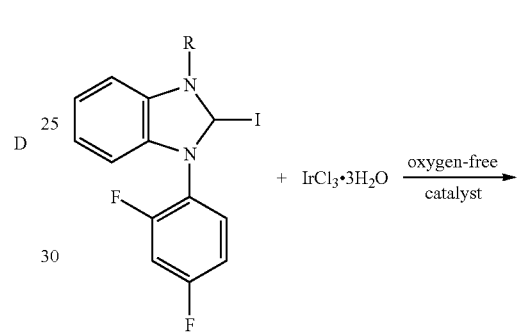
G

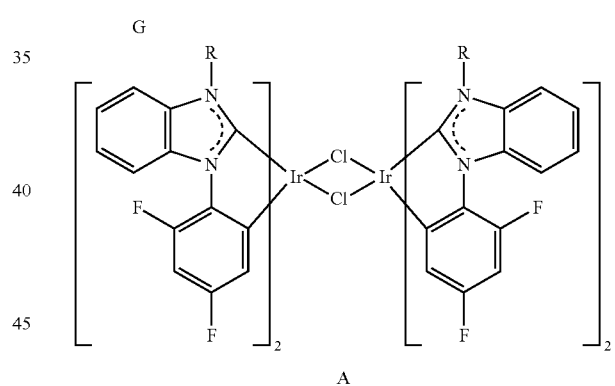
A

7. The preparation method of iridium-containing organic electroluminescent materials according to claim 6, wherein the Ullmann reaction in said step II is carried out in the temperature range of 100~180° C., using CuI or a mixture of 1,10-phenanthroline and CeCO3 as catalyst and N,N-dimethylformamide as solvent; the reaction in said step III is carried out in the temperature range of 25~45° C., using methylbenzene as solvent; the reaction in said step IV is carried out in the temperature range of 100~150° C., using Ag2O as catalyst and 2-ethoxyethanol as solvent.

8. The preparation method of iridium-containing organic electroluminescent materials according to claim 6, wherein said step II is followed by further separation and purification steps of compound E, which comprise: fisrtly, treating the mixed liquor obtained from the Ullmann reaction by vacuum concentration; then adding ethyl acetate solution to the concentrated liquor to form precipitate; filtering and separating the precipitate, then washing the precipitate by ethyl acetate, collecting the filter liquor; finally, concentrating the filter liquor which is then separated by silica gel column chromatography using mixed solvent of ethyl acetate and hexane as eluent to obtain compound E.

9. The preparation method of iridium-containing organic electroluminescent materials according to claim 6, wherein said step III is followed by further separation and purification steps of compound G, which comprise: filtering the rough production of step III, then washing the obtained precipitate by methylbenzene, drying to obtain purified compound G; said step IV is followed by further separation and purification steps of compound A, which comprise: firstly, treating the mixed liquor obtained from the reaction between compound G and iridium trichloride hydrate by decompression concentration, then separating the concentrated liquor 2~3 times by silica gel column chromatography using dichloromethane as eluent to obtain purified said compound A.

10. An organic electroluminescent device including a luminescent layer, said luminescent layer contains compound H represented by the following formula:

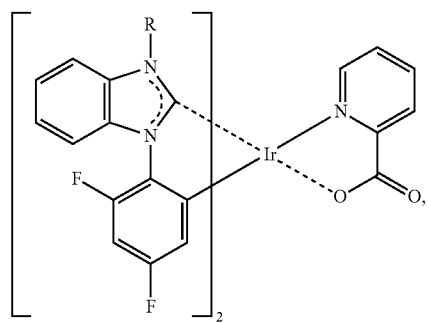

wherein R is C1-C8 alkyl.

* * * * *